(12) United States Patent
Boettger et al.

(10) Patent No.: US 10,846,851 B2
(45) Date of Patent: *Nov. 24, 2020

(54) METHOD AND SYSTEM FOR OUTPUTTING AUGMENTED REALITY INFORMATION

(71) Applicant: Siemens Healthcare GmbH, Erlangen (DE)

(72) Inventors: Thomas Boettger, Erlangen (DE); Christophe Della Monta, Heroldsbach (DE); Thilo Hannemann, Erlangen (DE); Philipp Hoelzer, Bubenreuth (DE); Gerhard Kraemer, Igensdorf (DE); Stefan Reichelt, Bamberg (DE); Grzegorz Soza, Heroldsberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/430,744

(22) Filed: Jun. 4, 2019

(65) Prior Publication Data

US 2019/0333213 A1   Oct. 31, 2019

Related U.S. Application Data

(63) Continuation of application No. 15/378,741, filed on Dec. 14, 2016, now Pat. No. 10,366,489.

(30) Foreign Application Priority Data

Dec. 23, 2015  (DE) .................. 10 2015 226 669

(51) Int. Cl.
  *G06T 7/00*  (2017.01)
  *A61B 90/30*  (2016.01)
  (Continued)

(52) U.S. Cl.
  CPC .......... *G06T 7/0012* (2013.01); *A61B 5/0013* (2013.01); *A61B 5/055* (2013.01);
  (Continued)

(58) Field of Classification Search
  CPC .......................... A61B 90/30; A61B 2090/365
  See application file for complete search history.

(56) References Cited

U.S. PATENT DOCUMENTS

| 2005/0206583 A1 | 9/2005 | Lemelson et al. |
| 2011/0238079 A1 | 9/2011 | Hannaford et al. |

(Continued)

FOREIGN PATENT DOCUMENTS

| CN | 103226817 A | 7/2013 |
| WO | WO-2015134958 A1 | 9/2015 |

(Continued)

OTHER PUBLICATIONS

Chinese Office Action dated Oct. 18, 2018 in Chinese Patent Application No. 2016112095800.

(Continued)

*Primary Examiner* — Ping Y Hsieh
*Assistant Examiner* — Jose M Torres
(74) *Attorney, Agent, or Firm* — Harness, Dickey & Pierce, P.L.C.

(57) ABSTRACT

A method and system are disclosed for outputting augmented reality information to a first user. In an embodiment, the method includes acquiring first information, including image information, depth information, coordinate information and combinations thereof, the first information relating to at least one of a medical device and a medical examination of a patient; creating the augmented reality information, relating to the medical device and/or the medical examination of the patient, based on the first information; and outputting the augmented reality information such that the (Continued)

augmented reality information is perceivable in a field of view of the first user.

35 Claims, 5 Drawing Sheets

(51) Int. Cl.
| | |
|---|---|
| *A61B 5/00* | (2006.01) |
| *G06F 3/01* | (2006.01) |
| *G06F 3/03* | (2006.01) |
| *G06F 3/0481* | (2013.01) |
| *G06F 3/0346* | (2013.01) |
| *G06T 7/50* | (2017.01) |
| *G06T 7/70* | (2017.01) |
| *A61B 5/055* | (2006.01) |
| *G06T 19/00* | (2011.01) |
| *A61B 90/00* | (2016.01) |
| *A61B 6/03* | (2006.01) |

(52) U.S. Cl.
CPC .............. *A61B 5/743* (2013.01); *A61B 5/745* (2013.01); *A61B 5/748* (2013.01); *A61B 90/30* (2016.02); *G06F 3/011* (2013.01); *G06F 3/012* (2013.01); *G06F 3/013* (2013.01); *G06F 3/0304* (2013.01); *G06F 3/0346* (2013.01); *G06F 3/04815* (2013.01); *G06T 7/50* (2017.01); *G06T 7/70* (2017.01); *G06T 19/006* (2013.01); *A61B 5/744* (2013.01); *A61B 6/032* (2013.01); *A61B 2090/365* (2016.02); *A61B 2576/00* (2013.01); *G06T 2207/30004* (2013.01); *G06T 2207/30204* (2013.01); *G06T 2210/41* (2013.01)

(56) References Cited

U.S. PATENT DOCUMENTS

| | | |
|---|---|---|
| 2011/0245660 A1 | 10/2011 | Miyamoto |
| 2013/0342851 A1 | 12/2013 | Dresel et al. |
| 2014/0002490 A1 | 1/2014 | Teegan |
| 2014/0098226 A1 | 4/2014 | Pletcher et al. |
| 2014/0275760 A1 | 9/2014 | Lee et al. |
| 2015/0234455 A1 | 8/2015 | LaValle et al. |
| 2015/0248793 A1 | 9/2015 | Abovitz et al. |
| 2015/0294507 A1 | 10/2015 | Teegan |
| 2016/0100760 A1 | 4/2016 | Ryu et al. |
| 2016/0249989 A1 | 9/2016 | Devam et al. |
| 2017/0042631 A1* | 2/2017 | Doo ..................... H04N 13/344 |

FOREIGN PATENT DOCUMENTS

| | | |
|---|---|---|
| WO | WO-2015/164402 A1 | 10/2015 |
| WO | WO-2015161307 A1 | 10/2015 |

OTHER PUBLICATIONS

Azuma, Ronald, et al. "Recent advances in augmented reality" in IEEE computergraphics and applications, 2001, 21, pp. 34-47.

Cakmakci, O., et.al.: "Head-Worn Displays: A Review", in: Journal of Display Technology, vol. 2, No. 3, pp. 199-216.

* cited by examiner

METHOD AND SYSTEM FOR OUTPUTTING AUGMENTED REALITY INFORMATION

PRIORITY STATEMENT

The present application is a continuation of and hereby claims priority under 35 U.S.C. § 120/121 to pending U.S. application Ser. No. 15/378,741 filed Dec. 14, 2016, which claims the benefit of priority under 35 U.S.C. § 119 to German patent application number DE 102015226669.9 filed Dec. 23, 2015, the entire contents of each of which are hereby incorporated herein by reference.

FIELD

At least one embodiment of the invention generally relates to a method for outputting augmented reality information, which relates to a medical device and/or to a medical examination of a patient, to a first user. At least one embodiment of the invention further generally relates to a system for outputting augmented reality information, to a computer program product and/or to a computer-readable medium.

BACKGROUND

A number of users with different specialist knowledge and perspectives are typically involved both in using a medical device, for example a medical imaging device, and also in a medical examination of a patient. These especially include patients, medical technicians, physicians with varying degrees of experience, technical staff and also makers of medical devices. Communication between these users is important for an efficient use of the medical device or for the success of the medical examination. In such cases there has previously been recourse to a great extent to verbal communication without any technical support. In addition known communication aids such as brochures, information sheets, information films, operating instructions etc. are used.

The medical examination of the patient can for example include an intervention, a therapy, in particular a radiation therapy, medical imaging, a clinical workflow, an instruction to the patient or similar.

In an intervention it is important to hit the target region precisely and to protect the surrounding healthy tissue. Therefore the intervention will be supported in many cases via medical imaging. Previously the transmission of the imaging information provided by way of the medical imaging to the intervention depended to a great extent on the capabilities, the experience and the spatial sense of the physician who is carrying out the intervention. Typically the imaging information provided by way of the medical imaging is displayed on one or more monitors. The monitor or the number of monitors is each arranged on a flexible support structure in an examination room in which the intervention is taking place. A relatively large distance between such a monitor and the intervention area can mean an enormous additional load for a physician, in particular when their ability to see the monitor is restricted. In addition the physician must often shift their view, in particular their focus, back and forth between the intervention area and the one or more monitors during the course of the intervention. In many cases this is also associated with an ergonomic load on the physician.

In a clinical workflow, for example in radiology, it is important that the patient receives clear instructions at the right time in order to pass through the various stations and steps efficiently. Further important aspects for a clinical workflow are the wellbeing of the patient, in particular in relation to anxieties, uncertainties and restrictions of the private sphere, as well as the protection of personal data. With medical imaging too timely and clear instructions, for example instructions affecting breathing, as well as the wellbeing of the patient are important.

SUMMARY

At least one embodiment of the invention includes at least one of an improved use of a medical device and an improved execution of a medical examination of a patient.

At least one embodiment of the invention is directed to a method, a system, a computer program product and/or a computer-readable medium.

In at least one embodiment of the inventive method for outputting augmented reality information, which relates to a medical device and/or to a medical examination of a patient, to a first user, first information is acquired, which is selected from the group that consists of image information, depth information, coordinate information and combinations thereof, wherein the first information relates to the medical device and/or to the medical examination. Based on the first information the augmented reality information, which relates to the medical device and/or the medical examination of the patient, is created. The augmented reality information is output such that the augmented reality information is able to be perceived in a field of view of the first user.

In accordance with one embodiment of the invention a movement parameter, which relates to a movement of a movable component of the medical device, can be acquired. Preferably the coordinate information is established based on the movement parameter. The movement parameter can in particular depend on a movement of the movable component. In particular the movement parameter can be a measure for a movement of the movable component. The movement parameter can for example specify a geometrical variable, in particular a location, a length and/or an angle. The movement parameter can for example specify an electric variable, in particular a current, a voltage, a charge and/or an energy. The electric variable can for example relate to a drive unit with which the movement of the movable component is driven.

In accordance with one embodiment of the invention, a medical dataset is provided by way of the medical device, wherein the augmented reality information is created based on the medical dataset. In accordance with one form of embodiment of the invention the medical dataset features a medical imaging dataset. In particular the medical imaging dataset can relate to a structure of the patient. In accordance with a further form of embodiment of the invention the medical dataset features a medical signal, which relates to the patient. The medical signal can for example be a physiological signal and/or a bioelectric signal. In particular the medical signal can relate to a heartbeat of the patient, breathing of the patient, a body temperature of the patient, a concentration of a substance in the blood of the patient or similar. The medical signal can for example be an electrocardiogram signal (EKG signal).

At least one embodiment of the inventive system for outputting augmented reality information, which relates to a medical device and/or to a medical examination of a patient, to a first user, features a first acquisition module, a creation module and a first output module. The first acquisition module is embodied for acquiring first information that is selected from the group that consists of image information, depth information, coordinate information and combinations thereof, wherein the first information relates to the medical device and/or the medical examination. The creation module is embodied for creating the augmented reality information that relates to the medical device and/or the medical examination of the patient, based on the first information. The first output module is embodied for outputting augmented reality information such that the augmented reality information is able to be perceived in a field of view of the first user.

One form of embodiment of the invention makes provision for the inventive system and/or for a number of components of the inventive system to be realized at least partly in the form of software on a processor system. In particular the first acquisition module, the creation module, the first output module, the information provision module, the second output module and the second acquisition module can each form a component of the inventive system and/or each be realized at least partly in the form of software on a processor system. One form of embodiment of the invention makes provision for the inventive system and/or a or a number of components of the inventive system to be realized at least partly in the form of software-supported hardware, for example FPGAs, a processor system or the like.

One form of embodiment of the invention makes provision for the inventive system and/or for a number of components of the inventive system to be formed at least partly by a Cloud via Cloud Computing. One form of embodiment of the invention makes provision for the creation module and/or at least a submodule of the creation modules to be formed by a Cloud via Cloud Computing. The Cloud can in particular feature a network of memory areas spatially remote from one another and processor systems spatially remote from one another. For data transfer from the Cloud and/or to the Cloud the first augmented reality device can feature a first Cloud interface and/or the second augmented reality device can feature a second Cloud interface.

The described method and the described system merely involve forms of embodiment of the invention. The invention can be varied by the person skilled in the art without departing from the area of the invention, provided it is specified by the claims.

BRIEF DESCRIPTION OF THE DRAWINGS

The invention will be explained once again in greater detail below with reference to the enclosed figures based on example embodiments. The representation in the figures is schematic and greatly simplified and also not absolutely true-to-scale.

In the figures.

DETAILED DESCRIPTION OF THE EXAMPLE EMBODIMENTS

Figure 1:
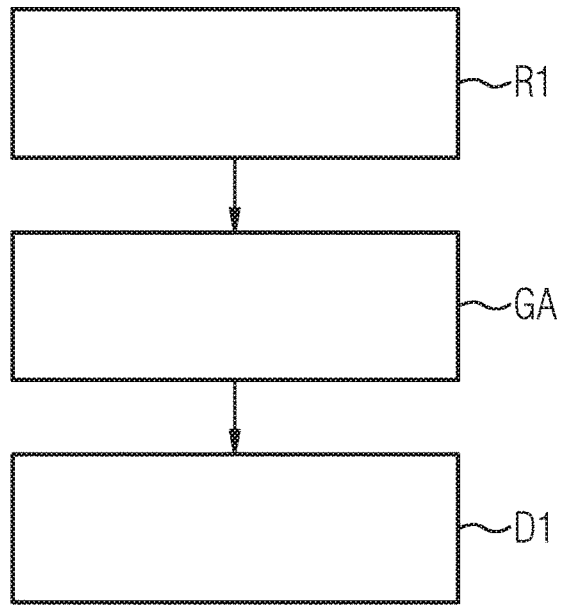
FIG. 1 shows a flow diagram of a method in accordance with a first form of embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group)

that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In at least one embodiment of the inventive method for outputting augmented reality information, which relates to a medical device and/or to a medical examination of a patient, to a first user, first information is acquired, which is selected from the group that consists of image information, depth information, coordinate information and combinations thereof, wherein the first information relates to the medical device and/or to the medical examination. Based on the first information the augmented reality information, which relates to the medical device and/or the medical examination of the patient, is created. The augmented reality information is output such that the augmented reality information is able to be perceived in a field of view of the first user.

Augmented reality information is especially to be understood as information with which a reality, in particular the field of view of the first user and/or a field of view of a second user, can be augmented. In particular an augmented reality can be created on the basis of the field of view of the first user and/or on the basis of the field of view of the second user with the augmented reality information. The augmented reality information is in particular able to be perceived in the field of view of the first user when the augmented reality information is visible for the first user in the field of view of the first user. In particular the augmented reality information can be output such that the field of view of the first user is augmented by the augmented reality information.

The augmented reality information can be created and/or output for example via an augmented reality device. The term "device for creating an augmented reality" and the term "augmented reality device" are used synonymously. An enhancement of a reality is known in particular to the person skilled in the art as "augmentation". An enhanced reality is known in particular to the person skilled in the art as "augmented reality". An enhanced reality device is known in particular to the person skilled in the art as an "augmented reality device".

A known device for creating an augmented reality is e.g. the Microsoft HoloLens® made by Microsoft Corporation, USA. The structure and the functioning of a device for creating an augmented reality are known to the person skilled in the art, in particular from US2014098226A1, US2015248793A1, US2015294507A1, US2015234455A1, WO2015134958A1, WO2015161307A1 and [CR06], the entire contents of each of which are hereby incorporated herein by reference.

One embodiment of the invention makes provision for the described method and/or one or more steps of the described method to each be carried out automatically or fully automatically. In particular the augmented reality information can be created automatically and/or fully automatically, in particular via the augmented reality device. "Automatically" in the context of the present application means that the respective step is carried out autonomously via software and/or via hardware and/or that essentially no interaction of a user is necessary for the respective step. Essentially no interaction of a user is necessary, particularly when one or more results are merely to be confirmed and/or one or more intermediate steps are merely to be carried out by a user. "Fully automatically" in the context of the present application means that no interaction at all of a user is needed for the execution of the respective step. Regardless of whether one or more steps are carried out "automatically" or "fully automatically", the inventive method can be an element of a workflow that additionally requires an interaction of a user. The interaction of the user can for example consist of the user manually creating or selecting an examination protocol and/or an examination plan and/or a clinical problem, from a menu presented via a screen for example.

As an alternative or in addition, the augmented reality information can be created on the basis of an input of the first user and/or based on an input of a second user. For example, based on an input of the first user and/or based on an input of the second user, a marking can be created and/or adapted in relation to a type, a position, a size and/or a shape, wherein the augmented reality information features the marking.

The image information can for example be a camera image and/or a 2D image (two-dimensional image). One form of embodiment of the invention makes provision for the first information to be a 3D image (three-dimensional image). The 3D image can in particular be a combination of a 2D image and depth information. In this case each pixel of the 3D image can be assigned an image value of the 2D image and a depth value of the depth information.

The image information can be acquired for example via a first camera unit. The first camera unit can be a 3D camera for example. The 3D image and/or the depth information can be acquired for example via the 3D camera. The first augmented reality device can for example feature the first camera unit. The 3D camera can be designed in particular for detection of electromagnetic radiation, in particular for detection of electromagnetic radiation in a lower-frequency range of the spectrum compared to x-ray radiation, for example in the visible or infrared range of the spectrum. The 3D camera can be embodied for example as a stereo camera or as a time-of-flight measurement system. A time-of-flight measurement system is known in particular to the person skilled in the art as a "time-of-flight camera". The 3D camera can be embodied for example for acquiring the 3D image and/or for acquiring the depth information by way of structured illumination.

The coordinate information can relate for example to a map dataset. The map dataset can for example feature a map of a spatial area in a field of view of the first user. In particular the at least one part of the medical device can be located in the spatial area and/or at least one part step of the medical examination can take place in the spatial area. The coordinate information can for example specify a position and/or an orientation in particular in relation to the map dataset and/or in relation to the map of the spatial area.

In accordance with one embodiment of the invention, the coordinate information comprises at least one patient coordinate, which relates to at least one part of the patient, and/or at least one device coordinate, which relates to at least one part of the medical device. The at least one patient coordinate can for example specify a position and/or an orientation of the at least one part of the patient, in particular in relation to the map dataset and/or in relation to the map of the spatial area. The at least one device coordinate can for example specify a position and/or an orientation of the at least one part of the medical device, in particular in relation to the map dataset and/or in relation to the map of the spatial area. The at least one part of the medical device can for example be a movable component of the medical device.

One form of embodiment of the invention makes provision for a position and/or a direction of view of the first user to be determined in particular in relation to the map dataset and/or in relation to the map of the spatial area and/or for a position and/or an alignment of the first augmented reality device to be determined in particular in relation to the map dataset and/or in relation to the map of the spatial area. The augmented reality information can be created for example based on the position and/or the direction of view of the first user and/or based on the position and/or the alignment of the first augmented reality device.

This can be done for example via the image information, via the depth information and/or via movement information.

The movement information can be acquired for example via one or more acceleration sensors. In particular the first augmented reality device can feature one or more acceleration sensors.

In a medical device, which has a patient support device with a transfer plate, the coordinate information can specify the position and/or the orientation of the transfer plate for example. In a medical device, which has a kinematic chain and/or a robot arm, in particular a C-arm, the coordinate information can specify the position and/or the orientation in each case for one or more elements of the kinematic chain and/or of the robot arm for example.

A plurality of different representations is conceivable for the coordinate information. There can be selection and/or transformation between these representations, without departing from the area of the invention, provided it is specified by the claims.

For example coordinate information that relates to a transfer plate, in a first representation can feature coordinates of four corner points of the transfer plate, in a second representation coordinates of a central point of the transfer plate as well as coordinates that specify the orientation of a plane approximately corresponding to the transfer plate, and in a third representation can feature one coordinate value, wherein the coordinate value is assigned a position and/or an orientation of the transfer plate, for example via a list, in particular a lookup table.

The coordinate information can for example be established by a position and/or an orientation being established, in particular measured. The coordinate information can for example be established by a position change and/or an orientation change being established, in particular measured.

In accordance with one embodiment of the invention the coordinate information is provided via the medical device.

The coordinate information can for example relate to a movable component of the medical device.

In accordance with one form of embodiment of the invention a device coordinate system is provided for the medical device. In this case the movable component can be controlled on the basis of the device coordinate system, for example via a control device of the medical device, in particular positioned and/or oriented. The coordinate information can for example comprise a device coordinate in relation to the device coordinate system.

One form of embodiment of the invention makes provision, during the creation of the augmented reality information, for a transformation of the coordinate information and/or of one of the coordinates included in the coordinate information, for example the device coordinate, to be carried out from a first reference system, for example the device coordinate system, into a second reference system, for example the map dataset. The transformation can be carried out for example based on transformation information that relates to the first reference system and the second reference system and/or with which coordinates of the second reference system can be assigned coordinates of the first reference system. For example the coordinate information can include the transformation information. Optionally the transformation information can be established and/or acquired.

With the aid of the coordinate information the augmented reality information can be created independently of the image information and/or independently of the depth information for example. In this case in particular a device coordinate system already provided for control of the medical device can advantageously additionally be used for creating the augmented reality information. In particular with the aid of the coordinate information in conjunction with a map dataset and/or a 3D model of the movable component and/or of the medical device, a position and/or an orientation of the movable component can be established very exactly and independently of visual circumstances. Optionally the coordinate information can be combined with the image information and/or with the depth information.

In accordance with one embodiment of the invention a control command, which relates to a movement of a movable component of the medical device, is output. Preferably the coordinate information is established based on the control command. A movement of the movable component can be controlled by way of the control command for example. In particular the control command can specify a target position, a position change, a target orientation, an orientation change and/or similar for the movable component. In particular coordinate information can be assigned to the control command and/or to the movement parameter.

In accordance with one embodiment of the invention a movement parameter, which relates to a movement of a movable component of the medical device, can be acquired. Preferably the coordinate information is established based on the movement parameter. The movement parameter can in particular depend on a movement of the movable component. In particular the movement parameter can be a measure for a movement of the movable component. The movement parameter can for example specify a geometrical variable, in particular a location, a length and/or an angle. The movement parameter can for example specify an electric variable, in particular a current, a voltage, a charge and/or an energy. The electric variable can for example relate to a drive unit with which the movement of the movable component is driven.

The movable component can for example be a C-arm, a robot arm, a kinematic chain, a transfer plate, an intervention tool or similar.

In accordance with one form of embodiment of the invention, the first information relates to a spatial area in a field of view of the first user. At least a part of the medical device can be located in the spatial area. At least a part step of the medical examination can take place in the spatial area. One form of embodiment of the invention makes provision for at least a part of the medical device to be located in a field of view of the first user and/or for at least a part step of the medical examination to take place in the field of view of the first user.

A part step of the medical examination can for example be a part step of an intervention and/or a part step of a clinical workflow. A part step of an intervention can for example be an introduction of an intervention tool and/or of an implant into the patient, a separation and/or a joining of a structure of the patient or similar. A part step of a clinical workflow can for example be calling a patient waiting in a waiting room, identifying the patient, clarify further steps of the clinical workflow for the patient, preparation of the patient in an examination room, instruction of the patient, preparation of the medical device, registration of the patient at the medical device, medical imaging, an intervention, a therapy, a diagnosis or similar.

In accordance with one embodiment of the invention, a medical dataset is provided by way of the medical device, wherein the augmented reality information is created based on the medical dataset. In accordance with one form of embodiment of the invention the medical dataset features a medical imaging dataset. In particular the medical imaging dataset can relate to a structure of the patient. In accordance with a further form of embodiment of the invention the medical dataset features a medical signal, which relates to the patient. The medical signal can for example be a physiological signal and/or a bioelectric signal. In particular the medical signal can relate to a heartbeat of the patient, breathing of the patient, a body temperature of the patient, a concentration of a substance in the blood of the patient or similar. The medical signal can for example be an electrocardiogram signal (EKG signal).

One form of embodiment of the invention makes provision for the augmented reality information to have an output field, wherein the medical dataset is represented in the output field. The medical dataset can be represented in the output field for example as a medical image, as a timing characteristic, as a signal curve and/or as a number.

One form of embodiment of the invention makes provision for a position of the medical device to be established relative to the field of view of the first user based on the first information, wherein the augmented reality information is created based on the position of the medical device. In this case, based on the position of the medical device, the position of the output field relative to the field of view of the first user can be determined. The output field can be displayed for example in the vicinity of the medical device and/or overlaid on the medical device. The output field can follow the medical device for example for a change of the position of the medical device relative to the field of view of the first user.

In accordance with one embodiment of the invention, examination information, which relates to the medical examination of the patient, is established based on the first information, wherein the augmented reality information is created based on the examination information.

The examination information can for example be information about which part steps of the medical examination have already been carried out and/or which part step is to be carried out as the next step. In particular the examination information can be established based on an examination plan, which comprises planned part steps of the medical examination, and/or based on an examination protocol. An examination plan can for example be an intervention plan and/or a flow plan of a clinical workflow. The examination information can for example involve a position of the patient relative to the medical device and/or a position of an intervention tool relative to a structure of the patient. For example the examination information can feature the information that an intervention tool is located in the correct position ready for use. The augmented reality information can feature a corresponding marking, which represents the next movement of the intervention tool to be carried out, for example in the form of a simulation.

In accordance with one embodiment of the invention patient information, which relates to the patient, is established based on the first information, wherein the augmented reality information is created based on the patient information.

In accordance with one embodiment of the invention the patient information is selected from the group that consists of Patient identification information, which relates to an identification of the patient, Patient state information, which relates to an physiological state and/or to an emotional state of the patient, Patient position information, which relates to a position of the patient, and combinations thereof.

The patient identification information is designed to identify the patient. The identification can in particular be carried out automatically and/or fully automatically. Based on the patient identification information for example, patient data of the patient can be selected from a patient database and/or output by way of the augmented reality information. The patient data can for example comprise personal data and/or data that relates to the patient history of the patient. In particular a check can be made in this way as to whether a given part step of the medical examination and/or which part step of the medical examination is planned for the patient. In particular the patient data and/or a result of the check can be output by way of the augmented reality information. Based on the patient identification information for example, data that will be acquired during the medical examination of the patient and/or by way of the medical device is automatically assigned to the patient and/or stored in a patient database. This thus enables incorrect examinations and incorrect assignments to be avoided.

The patient identification information can for example be established based on the image information, in that biometric features of the patient are established and/or in that a code, in particular a QR code, which is assigned to the patient and/or to a patient file of the patient, is acquired and evaluated.

The patient status information can for example relate to breathing of the patient, a body temperature of the patient, a pulse of the patient, a pupil dilation of the patient, a facial expression of the patient or similar. Based on the patient state information it can be established for example whether and/or to what degree the patient is exhibiting stress. A warning signal can be output by way of augmented reality information for example if the stress of the patient could adversely affect the success of the medical examination. The augmented reality information can for example feature a calming image and/or a sequence of calming images for calming the patient.

The position of the patient can for example be selected from the patient position group, which consists of a position of the patient in a clinic, a position of the patient in an examination room, a position of the patient relative to the medical device, a position of the patient relative to the first user, a position of the patient relative to the second user and combinations thereof. The augmented reality information can for example be created based on the patient position information such that the position of the augmented reality information relative to the field of view of the first user is determined based on the position of the patient. The augmented reality information can for example be shown in the vicinity of the patient and/or overlaid on the patient. The augmented reality information can for example follow the patient for a change of position of the patient relative to the field of view of the first user.

In accordance with one embodiment of the invention a medical imaging dataset, which relates to a structure of the patient, is provided, wherein the augmented reality information is created based on the medical imaging dataset. In accordance with one aspect of the invention the augmented reality information features a structure marking that marks the structure of the patient. The medical imaging dataset can be provided for example by way of the medical device, in particular by way of a medical imaging device, and/or by way of a medical image database. In particular the medical image database can feature a memory area in which the medical image dataset is held for retrieval.

The structure of the patient can for example be an anatomical structure of the patient. The structure of the patient can for example feature an organ of the patient and/or an implant of the patient. The implant can for example be a screw, a prosthesis, a vessel prosthesis, a heart valve prosthesis or similar. The structure marking can for example feature a medical image of the structure of the patient and/or be shown overlaid in the field of view of the first user on the structure of the patient. The medical image of the structure can be segmented into part structures for example. In such cases the structure of the patient does not necessarily have to be visible. For example based on the first information and/or based on further information, for example a topogram and/or anatomical landmarks, a position of the structure relative to the patient and/or a position of the structure marking relative to the field of view of the first user, which corresponds to the position of the structure relative to the patient, is established. The structure marking can for example feature a 3D image of the structure and/or a 3D model of the structure. With the aid of the structure marking for example the medical examination, in particular an intervention, can be planned and/or supported. The structure marking can for example feature a three-dimensional rendered image of the structure and/or an unfolding representation of the structure.

For improved visualization of medical problems or circumstances, a computer-generated image can be overlaid on the patient in the correct location. In this way an in particular three-dimensionally rendered image of a structure, in particular of an inner anatomy, of the patient can be overlaid on the patient for example. With such an image for example a path of an interventional procedure and/or for one or more sections of a vessel a diagnostic value in each case, e.g. a fractional flow reserve (FFR), can be displayed. For example by way of the augmented reality information an unfolding representation of the rib cage of the patient can be shown overlaid on the rib cage of the patient.

One form of embodiment of the invention makes provision for anatomical landmarks based on the first information and/or based on the medical imaging dataset to be detected and/or used as orientation points. Based on the anatomical landmarks the rendered image can be registered in relation to the patient and/or in relation to the structure of the patient. The rendered image is thus able to be shown overlaid on structure of the patient.

In accordance with one embodiment of the invention nominal position information, which relates to a nominal position of the patient and/or a nominal position of the medical device, is provided, wherein the augmented reality information is created based on the nominal position information, wherein the augmented reality information features a nominal position marking, which marks the nominal position of the patient and/or the nominal position of the medical device.

The nominal position information then relates in particular to a nominal position of the medical device, if the nominal position information relates to a nominal position of the movable component of the medical device. The nominal position information can for example be established based on a pre-examination, based on an examination plan and/or based on an examination protocol of the medical examination. The examination protocol can in particular be an imaging protocol. The nominal position information can for example specify how the patient is to be positioned for the medical examination and/or relative to the medical device. The nominal position information can for example specify how the medical device and/or the movable component are to be positioned relative to the patient and/or relative to the examination room. The nominal position marking can for example feature a 3D avatar of the patient, wherein the 3D avatar shows the patient in the nominal position of the patient. The nominal position marking can for example feature a 3D model of the medical device and/or of the movable component, wherein the 3D model shows the medical device in the nominal position of the medical device and/or the movable component in the nominal position of the movable component.

In accordance with one embodiment of the invention region information, which relates to a region of the patient and/or a region of the medical device, is provided, wherein the augmented reality information is created based on the region information, wherein the augmented reality information features a region marking that marks the region of the patient and/or the region of the medical device.

The region of the patient can for example feature the structure of the patient. The region of the patient can for example be a region of the patient that is to be examined in the medical examination and/or that is selected for the medical examination. The region of the patient can for example be a region of the patient that is located in the effective region of the medical device and/or that is selected for a transfer into the action region of the medical device. The action region of the medical device can for example be an action region of an intervention tool, a raw image data acquisition region of a medical imaging device or similar. The region of the patient can for example be a region of the patient in which an intervention is to be carried out and/or from which a medical imaging dataset is to be recorded. The region of the medical device can for example be a region of the medical device, which is to be used and/or actuated. The region marking can for example feature a 3D image of the regions of the medical device and/or a 3D model of the regions of the medical device. This enables the operation of the medical device, for example in the medical examination and/or in a preparation of the medical device, to be planned and/or supported.

In accordance with one form of embodiment of the invention, based on an input of the first user and/or based on an input of the second user, the region information can be created and/or the region marking can be adapted in relation to a type, a position, a size and/or a shape. One form of embodiment of the invention makes provision for the region information to be established based on an examination plan, based on an examination protocol of the medical examination, based on the patient position information and/or based on the nominal position information.

In accordance with one embodiment of the invention a marking, which is selected from the markings group, which consists of the structure marking, the nominal position marking, the region marking and combinations thereof, features a representation which is selected from the representation group, which consists of a hologram, a hologram-type representation, a stereoscopic representation, a three-dimensional representation and combinations thereof. This in particular enables a 3D avatar, a 3D image and/or a 3D model to be represented in an especially advantageous manner. A hologram-type representation can especially be understood as a visual representation, which gives an observer, for example the first user and/or the second user, the impression that they are looking at a hologram.

In accordance with one embodiment of the invention an input of the first user is detected, wherein the augmented reality information is created based on the input of the first user. In particular a marking, which is selected from the marking group, which consists of the structure marking, the nominal position marking, the region marking and combinations thereof, can be created based on the input of the first user and/or adapted in relation to a type, a position, a size and/or a shape.

One embodiment of the invention makes provision for the augmented reality information to be output such that the augmented reality information is able to be perceived in a field of view of a second user, that an input of the second user is detected and that the augmented reality information is created based on the input of the second user.

The augmented reality information is in particular able to be detected in the field of view of the second user when the augmented reality information is visible in field of view of the second user for the second user. In particular the augmented reality information can be output such that the field of view of the second user is enhanced by the augmented reality information. In accordance with one form of embodiment of the invention at least a part of the field of view of the first user is shown in a field of view of the second user. In accordance with one form of embodiment of the invention at least the part of the field of view of the first user is shown in the field of view of the second user such that the second user sees the patient and/or the medical device from the perspective of the first user. In accordance with one form of embodiment of the invention the augmented reality information is shown in the field of view of the second user such that the second user sees the augmented reality information from the perspective of the first user.

In particular, the features that are described in relation to the first user and without reference to the second user also apply correspondingly in relation to second user, i.e. when in the features the term "first user" is replaced by the term "second user" in each case. In particular, a marking that is selected from the marking group which consists of the structure marking, the nominal position marking, the region marking and combinations thereof, can be created based on the input of the second user and/or adapted in relation to a type, a position, a size and/or a shape. In accordance with one aspect of the invention the nominal position information and/or the region information can be established based on the input of the first user and/or based on the input of the second user.

Preferably the input of the first user is a gesture of the first user and/or the input of the second user is a gesture of the second user.

In accordance with one embodiment of the invention a first user profile, which relates to the first user, and/or a second user profile, which relates to the second user, is selected, wherein the augmented reality information is created based on the first user profile and/or based on the second user profile.

The user profile can for example comprise a user category, a function in the medical examination, an access authorization to patient data of the patient, a usage authorization for the medical device, an authorization that relates to the creation, changing, overwriting and/or removal of the augmented reality information, or similar. The user category can relate for example to a group of people. Optionally a group of people can be assigned respectively to the first user and/or the second user. Groups of people can for example be patients, medical technicians, physicians of different levels of experience, technicians and also makers of medical device. The function in an intervention can for example be selected from a function group consisting of the first physician who carries out the intervention on their own, a second physician who carries out the intervention under instruction, a third physician who observes the intervention and learns in doing so, and a fourth physician who observes the intervention and in doing so gives instructions for carrying out the intervention.

One form of embodiment of the invention makes provision for the augmented reality information to be created based on the first information and based on basic information. The basic information can for example be selected from the basic information group, which consists of the medical dataset, the examination information, the patient information, the medical imaging dataset, the nominal position information, the region information, the input of the first user, the input of the second user, the first user profile and the second user profile.

One form of embodiment of the invention makes provision for the augmented reality information to be created based on the first information and based on a number of items of basic information. Each of the number of items of basic information can for example be selected in each case from the basic information group, which consists of the medical dataset, the examination information, the patient information, the medical imaging dataset, the nominal position information, the region information, the input of the first user, the input of the second user, the first user profile and the second user profile.

In the context of the present application the expression "based on" can be understood in particular in the sense of the expression "when using". In particular a formulation in accordance with which a first feature is created based on a second feature (alternatively: established, determined etc.) does not exclude that the first feature is created (alternatively: established, determined etc.) based on a third feature.

At least one embodiment of the inventive system for outputting augmented reality information, which relates to a medical device and/or to a medical examination of a patient, to a first user, features a first acquisition module, a creation module and a first output module. The first acquisition module is embodied for acquiring first information that is selected from the group that consists of image information, depth information, coordinate information and combinations thereof, wherein the first information relates to the medical device and/or the medical examination. The creation module is embodied for creating the augmented reality information that relates to the medical device and/or the medical examination of the patient, based on the first information. The first output module is embodied for outputting augmented reality information such that the augmented reality information is able to be perceived in a field of view of the first user.

In accordance with one embodiment of the invention the system features the medical device. Preferably the medical device is embodied for providing the coordinate information.

In accordance with one embodiment of the invention the medical device features a movable component.

In accordance with one form of embodiment of the invention the system and/or the medical device features a control device that is embodied for output of a control command, which relates to a movement of the movable component. In accordance with one form of embodiment of the invention the system features a movement parameter acquisition unit that is embodied for acquiring a movement parameter that relates to a movement of the movable component. The movement parameter acquisition unit can for example feature a sensor. The movement parameter can be acquired for example via the movement parameter acquisition unit.

One form of embodiment of the invention makes provision for the movable component to be able to be controlled, in particular positioned and/or oriented, via the first augmented reality device and/or via the second augmented reality device.

In accordance with one form of embodiment of the invention the medical device features a drive unit that is embodied to drive a movement of the movable component. Preferably the drive unit is embodied for receiving the control command and/or for driving a movement of the movable component based on the control command. The drive unit can be embodied as an electric motor for example. The movement parameter can for example specify an electric charge consumed by the drive unit when driving the movement and/or electric energy consumed by the drive unit when driving the movement.

The movement parameter acquisition unit can be integrated for example into the control device and/or into the drive unit. The movement parameter acquisition unit can be embodied for example for measuring the movement parameter. The movement parameter can for example specify a rotational speed angle, in particular a number of revolutions. The movement parameter can for example be a measure for the movement of the movable component and/or relate to the movable component, the drive unit and/or the movement parameter acquisition unit. In particular a calibration and/or a simulation of the medical device and/or of the control device and/or of the movable component and/or the drive unit and/or a movement of the movable component can be carried out.

Preferably the system features an establishment unit, which is embodied for establishing the coordinate information based on the control command and/or based on the movement parameter. The coordinate information can for example be established via the establishment unit based on the control command and/or based on the movement parameter.

In accordance with one form of embodiment of the invention the first acquisition module features a first camera unit, wherein the first camera unit is embodied for acquiring the image information and/or the depth information. In accordance with a further form of embodiment of the invention the first acquisition module can access a memory area of an information provision module, wherein the first information is acquired via a data transfer from the information provision module to the first acquisition module. In accordance with one form of embodiment of the invention the system features the information provision module. The information provision module is embodied for providing the first information.

In accordance with one form of embodiment of the invention the first output module is embodied for outputting the augmented reality information such that the field of view of the first user is enhanced by the augmented reality information. In accordance with one form of embodiment of the invention the first output module features a first viewing device, in particular in the form of data eyeglasses, a data contact lens and/or a retinal projector. In particular the augmented reality information can be output by way of the first viewing device. In accordance with a further form of embodiment of the invention a first viewing device can access a first memory area of the first output module, wherein the augmented reality information will be output via a data transfer by the first output module to the first viewing device. In accordance with one form of embodiment of the invention the system features the first viewing device.

In accordance with one embodiment of the invention the system features the medical device, wherein the medical device is embodied for provision of a medical dataset. Preferably the creation module is embodied for creating the augmented reality information based on the medical dataset.

In accordance with one embodiment of the invention the system features a medical imaging device, wherein the medical imaging device is embodied for provision of a medical imaging dataset, which relates to a structure of the patient. Preferably the creation module is embodied for creating the augmented reality information based on the medical imaging dataset. Preferably the augmented reality information features a structure marking, which marks the structure of the patient.

In accordance with one embodiment of the invention the system features a first input module, which is embodied for acquiring an input of the first user, and/or a second input module, which is embodied for acquiring an input of the second user. Preferably the creation module is embodied for creating the augmented reality information based on the input of the first user and/or based on the input of the second user.

One form of embodiment of the invention makes provision for the first acquisition module to feature the first input module and/or for the first acquisition module to be embodied for acquiring an input of the first user and/or for the first camera unit to be embodied for acquiring the input of the first user. In accordance with one aspect of the invention the system features a second output module and a second acquisition module. The second output module is embodied for output of the augmented reality information such that the augmented reality information is able to be perceived in a field of view of a second user. One form of embodiment of the invention makes provision for the second acquisition module to feature the second input module and/or for the second acquisition module to be embodied for acquiring the input of the second user and/or for the second camera unit to be embodied for acquiring the input of the second user.

In accordance with one form of embodiment of the invention the second output module is embodied for showing at least a part of the field of view of the first user in a field of view of the second user. In accordance with one form of embodiment of the invention the second output module is embodied for output of the augmented reality information such that the field of view of the second user is enhanced by the augmented reality information.

In accordance with one form of embodiment of the invention the second output module features a second viewing device, in particular in the form of data eyeglasses, a data contact lens and/or a retinal projector. In particular the augmented reality information can be output by way of the second viewing device. In accordance with a further form of embodiment of the invention a second viewing device can access a memory area of the second output module, wherein the augmented reality information will be output via a data transfer by the second output module to the second viewing device. In accordance with one form of embodiment of the invention the system features the second viewing device.

In accordance with one form of embodiment of the invention the second acquisition module features a second camera unit, wherein the second camera unit is embodied for acquiring the input of the second user. In accordance with a further form of embodiment of the invention the second acquisition module can access a memory area of an input provision module, wherein the input of the second user is acquired via a data transfer from the input provision module to the second acquisition module. In accordance with one form of embodiment of the invention the system features the input provision module.

In accordance with one embodiment of the invention the system features a first augmented reality device, which features the first acquisition module and/or the first output module. The first augmented reality device can for example be embodied as data eyeglasses and/or a data headset. The first augmented reality device can for example be wearable and/or worn by the first user. In accordance with one form of embodiment of the invention the first augmented reality device features the creation module.

In accordance with one embodiment of the invention the system features a second augmented reality device, which features the second acquisition module and/or the second output module. The second augmented reality device can for example be embodied as data eyeglasses and/or a data headset. The second augmented reality device can for example be wearable and/or worn by the second user. In accordance with one form of embodiment of the invention the second augmented reality device features the creation module.

One form of embodiment of the invention makes provision for the creation module to feature a first creation submodule and a second creation submodule, for the first augmented reality device to feature the first creation submodule and for the second augmented reality device to feature the second creation submodule.

One form of embodiment of the invention makes provision for the augmented reality information to be created via a machine-learning algorithm. The machine-learning algorithm can for example evaluate the first information, the examination information, the patient information, the nominal position information, the region information, the input of the first user and/or the input of the second user.

In accordance with one embodiment of the invention the system features a user profile selection module. The user profile selection module is embodied for selection of a first user profile, which relates to the first user, and/or for selection of a second user profile, which relates to the second user. Preferably the creation module is embodied for creation of the augmented reality information based on the first user profile and/or based on the second user profile. The user profile selection module can for example provide a graphical user interface, wherein the first user profile and/or the second user profile can be set up and/or selected by way of the graphical user interface. In accordance with one form of embodiment of the invention the user profile selection module has a security interface for acquiring a security certificate. The security certificate can in particular be a password and/or a hardware key, for example a smart card. In particular this enables access to the first user profile and/or access to the second user profile to be protected.

In accordance with one embodiment of the invention the system is embodied for carrying out an inventive method for outputting augmented reality information, which relates to a medical device and/or a medical examination of a patient.

In particular, an embodiment of the invention make communication between a number of users possible, in particular improving communication between a number of users from different groups of people that are involved in using a medical device and/or involved in a medical examination of a patient. For a user of a device for creating an augmented reality, additional (audio)-visual elements can be added to the real world that he or she perceives in their field of vision, existing elements can be edited out and/or changed in their appearance. In addition images and sound can be picked up from the perspective of the user and/or the direction of view of the user can be determined.

This information can be provided to one or more further users of another device in each case for creating an augmented reality, in particular as augmented reality information. In this case the augmented reality information can be provided at the same location or provided at another remote location by remote data transmission. The augmented reality information and/or the created augmented reality can be used in order to support communication between the users involved in using a medical device, for example a medical imaging device, and/or involved in a medical examination. The user can for example be selected from the user group that consists of the first user and the second user. The user or the number of further users can be selected in each case from the user group that consists of the first user and the second user.

One application of medical imaging lies in the field of intervention, in which the images provided by the medical imaging device are used during a medical intervention in order to plan the intervention and to check the progress of the intervention. This type of use of the medical imaging device in many cases makes high demands on the physician and requires a high level of training, in which typically an experienced physician passes on his or her knowledge to a more inexperienced physician. The communication between the two physicians is able in this case to be supported by a device for creating an augmented reality so that the experienced physician observes the images recorded from the perspective of the inexperienced physician and can insert tips as to how to proceed further directly into the field of view of the inexperienced physician. In this case the inexperienced physician wears a device for creating an augmented reality, while the experienced physician either likewise wears such a device or uses a conventional device for information processing, e.g. a laptop or a tablet. One form of embodiment of the invention makes provision for the first input module and/or the second input module in each case to feature a mouse, a joystick, a touchpad, a touch-sensitive input device and/or similar.

The experienced physician could for example, during an intervention for ablation, display the nominal position of the ablation needle on the patient and thus instruct the inexperienced physician. Likewise the roles could be reversed and the experienced physician could undertake the intervention. Then the inexperienced physician could observe the intervention from the perspective of the experienced physician and thus learn by example. In this case it is of no significance whether the experienced and inexperienced physician are located in the same room, so that this instruction can also be done "remotely", i.e. by remote transmission. To this end it is useful for there also to be a bidirectional transmission of audio signals as well as the transmission of the augmented reality information, so that the two physicians can talk to each other. It is not absolutely necessary for the inexperienced physician to place himself or herself in the perspective of the experienced physician simultaneously with the carrying out of the intervention. For example the first information and/or the augmented reality information can be recorded and/or enhanced with additional information inserted during the medical examination or retrospectively and made available to the inexperienced physician at a later time.

One embodiment of the invention makes provision for the support of an inexperienced physician by an experienced physician to take place not in the sense of training but during normal operation. Thus an experienced physician could be available on demand as an expert in order to support physicians, e.g. in rural regions, when complications occur or in especially complicated cases. In particular the experts could support a physician in carrying out biopsies supported by imaging. This support could also be provided in advance of the intervention, in order to determine the best possible access for the intervention. For example the expert could assist the physician in the planning of the intervention path on the basis of the medical imaging dataset.

An embodiment of the invention in particular makes it possible to support the conversation between the patient and a physician. This can take place before an intervention for example, wherein the physician explains to the patient in the augmented reality and/or by way of the augmented reality information the execution or the results of the intervention or visualizes the risks. Likewise the physician can show the patient the results of the examination in the augmented reality and/or by way of the augmented reality information after the intervention has been performed.

In such cases it can be advantageous to show these to the patient in a "virtual mirror". It is actually also conceivable to show the patient the result of an examination by way of inserting the augmented reality information directly at the examined point on their body. However on the one hand this can be complicated for the patient or not able to be seen at all (e.g. for the spinal column). On the other hand it can be very disconcerting for the patient if this representation of the result is too realistic. Therefore it can be advantageous not to insert this representation of the result on the patient himself or herself, but on a "virtual mirror", i.e. a surface within their augmented reality, which shows the patient similar to a mirror image and into which the result of the examination can be inserted. As an alternative or in addition a monitor together with a camera can be used for this representation of the result.

An embodiment of the invention makes improved instruction of the patient before and/or during the medical examination possible for example. For the patient the medical examination, which can be carried out with the medical device for example, typically represents an exceptional situation. In general the patient possesses little knowledge about the procedures in the clinic and during the examination.

Communication between the clinic personnel and the patient can be supported by the use of a device for creating an augmented reality. To this end the patient can for example be guided through the clinic to the location of the examination by augmented reality information inserted into his or her field of view, e.g. arrows on the floor. At the location of the examination he or she can be shown by way of the augmented reality information, in particular in the form of audiovisual information, whether he or she still has to wait, how many patients there are before him or her, how long the waiting time is likely to be and which examination room he or she should go to for the examination. Within the framework of the preparation for the examination he or she can be instructed by way of the inserted augmented reality information, in particular in the form of audiovisual information, to take off his or her clothing in accordance with the examination and/or to put on other clothing. The patient can further be instructed to take up a particular pose in the examination room, e.g. to lay down in a particular orientation on the examination couch and/or to raise his or her arms. This can also be supported by a "virtual mirror" in which the patient sees himself or herself and/or an avatar of himself or herself in a mirror generated in the augmented reality. After a part step of the examination he or she can be instructed as to the way in which he or she can leave the examination room and/or be guided for a further part step of the examination, for example in another examination room.

A particular advantage of the use of a device for creating an augmented reality lies in the fact that the augmented reality information can be tailored to the individual patients and a number of patients in the same room can each perceive their individual augmented reality information, e.g. for the instruction as to which examination room they should go to. A further advantage lies in the fact that confidentiality is better preserved when each patient can only perceive the instructions that are intended for him or her and e.g. calling the patient by name in the waiting room can be dispensed with.

An embodiment of the invention further makes possible improved support of personal communication between the patient and the operating personnel of a medical device. During a CT or MRT examination it is often not possible for the operating personnel to remain with the patient all the time. Instead, with CT for reasons of radiation protection for example, they withdraw from the examination room into a control room. By way of augmented reality information the presence of the operating personnel in the examination room, for example simultaneously with a bidirectional sound transmission, can be shown for the patient. By way of augmented reality information the patient can be shown as an element of the augmented reality within the control room for the operating personnel.

The bidirectional sound transmission can be undertaken by way of an intercom system for example. As an alternative or in addition the bidirectional sound transmission can be modified in real time, e.g. by in particular simultaneous machine translation. In this way the patient and the operating personnel can understand one another even if they do not speak a common language.

Through these applications of augmented reality the patient does not feel left alone during the examination and his or her anxieties can be reduced. It is possible in particular, by way of the augmented reality information, to display the operating personnel embodied by an avatar for the patient in the examination room. The avatar could e.g. be present constantly. The operating personnel can for example only be linked to the avatar when a patient situation demanding attention, for example noises and/or movements, is detected via sensors. In this way the operating personnel can go about their work, while for the patient on the other hand the feeling of a constant presence is produced, which helps to reduce his or her tension and anxieties.

An embodiment of the invention in particular makes it possible to support the operating personnel, e.g. in the placement of the patient, in the selection of support aids or in the placement of EKG electrodes or devices for measuring the breathing. In such cases this support can be provided on the one hand by another person, e.g. an application specialist of the maker, who inserts information for placement and/or selection for the operating personnel by way of the augmented reality information. On the other hand the augmented reality information can be created automatically for example on the basis of the specifications of the maker, which can be adapted additionally to the specific requirements of the individual clinic, e.g. on the basis of the selected measurement protocol of the medical device or on the basis of other data. This other data can be anatomical landmarks of the patient for example. Anatomical landmarks can be established in particular based on the image information and/or based on the depth information. The optimum position of EKG electrodes can be computed via anatomical landmarks for example.

Thus the communication from the maker to the user, which would otherwise be undertaken above all by training and by the operating instructions, can be supported by way of the augmented reality information.

An embodiment of the invention in particular makes possible improved training of the operating personnel. To this end for example a virtual patient can be introduced by way of augmented reality information into the augmented reality of the operating personnel to be trained, wherein an examination can be carried out as a exercise with the virtual patient. The virtual patient in this case can be fully computer-generated, i.e. also generated by inputs of a further person, e.g. likewise with the aid of a device for creating an augmented reality. This procedure offers the advantage, in particular with x-ray devices, that in this way, even when conducting a training exercise, the triggering of the x-ray radiation can be simulated. Conducting training exercises with real patients, in particular because of the radiation load, would be associated with severe restrictions.

In accordance with one form of embodiment of the invention the first augmented reality device features a first camera unit, wherein the first camera unit is embodied for acquiring the image information and/or the depth information.

One form of embodiment of the invention makes provision for the first augmented reality device to be embodied as data eyeglasses. Such data eyeglasses can be worn by the user for example. The user can for example be a radiologist or an assistant medical technician. In one form of embodiment of the invention an image of the patient is acquired via the first camera unit. This image is compared with entries in a patient database. This enables it to be established which patient is involved and/or whether there is a match with the planned examination. Such an identification check enables incorrect examinations and incorrect assignments of examination results to be avoided.

In a further variant of an embodiment of the invention information, annotations and/or images from a pre-examination of the patient are transferred to the user by way of the augmented reality information and/or made available in an augmented reality.

By a clever presentation and an interactive interaction with the data presented by way of the augmented reality information (images, histology, blood values etc.) the user can very quickly generate a holistic overall picture of the patient.

Based on the patient information, in particular based on the patient identification information, patient history information that relates to a patient history of the patient can be established.

Based on the patient information for example characteristic features of the patient can be established. For example with the aid of a database in which reference datasets are stored, based on the patient information, a suitable reference dataset can be established, which can be used for example for dose modulation in a medical examination with ionizing radiation.

A medical image, which was established for example within the framework of a pre-examination, for example as a 3D model of the body region of the patient, which corresponds to the medical image, can be shown projected-on and/or overlaid by way of the augmented reality information. In this way the user can recognize quickly and accurately whether diagnostically relevant information is already present at a particular, for example painful, point.

One form of embodiment of the invention makes provision for the patient to be recognized based on the image information, for patient information and/or patient data to be established based on the first information and to be made available by way of the augmented reality information. That can be advantageous in particular when an emergency physician is deployed to the scene of an accident.

In accordance with a further form of embodiment of the invention the augmented reality information is presented location-specifically in the field of view of the user. For example a diagnostic display, which is arranged in an examination room, in particular an OP room, can be enhanced by the augmented reality information. The augmented reality information can for example feature an EKG signal, a breath curve, a patient history, biological data of the patient. The augmented reality information can in particular be output during viewing of the medical device and/or of the diagnostic display.

In another form of embodiment of the invention the user, for example a radiologist, an assistant medical technician or a nursing sister, will be equipped with a device for creating an augmented reality, e.g. in the form of data eyeglasses. Preferably a unique feature, able to be evaluated automatically, for example a QR code, is arranged on the patient and/or on the patient file. When this feature is looked at a virtual ticket can be shown as augmented reality information for example. The user can thus see the current information that relates to the patient.

A further form of embodiment of the invention makes provision for the user to be able to log on to an account generated for the user. With the account a user profile of the user, which in particular includes rights of the user, can be managed for example. In this way exclusively that information and/or those images for which the user is authorized and/or which relate to a patient assigned to the user can be output, in particular by way of augmented reality information.

The first information can for example feature a topogram, in particular a camera-based topogram. In particular the topogram can be a combination of image information and depth information. In accordance with one form of embodiment of the invention a camera-based topogram is acquired via a first camera unit, which is integrated for example into the first augmented reality device. The camera-based topogram can for example be shown overlaid by way of the augmented reality information on the patient. Above and beyond this characteristic features of the patient can be established based on the camera-based topogram. With the aid of a database in which reference datasets are held, a suitable reference data for the medical examination can thus be established based on the camera-based topogram, which can be used for example for dose modulation.

In accordance with one form of embodiment of the invention patient status information is transferred to the user by way of the augmented reality information. The patient status information can for example be a facial expression of the patient, a body temperature of the patient, a pupil dilation of the patient and/or similar. The patient status information can for example relate to emotional indicators, which in particular can point to stress of the patient. By way of augmented reality information for example one or more physiological parameters of the patient can be displayed, in particular a pulse, a breathing rhythm and/or similar.

One form of embodiment of the invention makes provision for the patient information, for example immediately before an intervention, to be acquired via the data eyeglasses, for the acquired patient information to be compared with entries in a database, for a matching entry from the database, for example based on similar bodily features of the patient and/or based on a similar intervention, to be established and for an intervention result assigned to the matching entry to be shown projected and/or overlaid onto the surface of the patient. In this way a better impression of the result of the intervention to be expected can be imparted to the user, in particular a radiologist and/or surgeon.

In accordance with a further form of embodiment of the invention the patient is equipped with data eyeglasses. Physiological parameters of the patient, such as e.g. heartbeat, which allow an impression of the emotional state of the patient to be obtained, can be acquired. If these physiological parameters point to the patient being under stress, a calming environment serving to relieve stress can be displayed via the data eyeglasses. For example countryside that suggest wide-open spaces can be shown to a patient who suffers from claustrophobia to be examined with a medical imaging device. As an alternative or in addition examination-relevant instructions, e.g. breathing commands, can be displayed via the data eyeglasses. Furthermore audio signals can also be used.

In accordance with one form of embodiment of the invention virtual, for example computer-generated, data, which relates to the medical examination, can be shown overlaid on the patient by way of the augmented reality information. Thus a better ability to conceive and carry out a medical examination is especially able to be realized.

With a device for creating an augmented reality, in particular medical images, e.g. DICOM images, and additional information can be shown overlaid on the patient by way of the augmented reality information. The use of a device for creating an augmented reality for a medical examination, for example for an intervention, makes possible enormous improvements in particular in relation to the visualization, the display of information and the provision of virtual processing tools, in particular image processing tools.

The medical imaging dataset can for example feature a medical image, in particular a DICOM image, a CT image, an MRT image, an ultrasound image, an angiography image series, an endoscopy video or similar. The augmented reality information can feature the medical imaging dataset and/or a marking that was established based on the medical imaging dataset. Thus the medical imaging dataset and/or the marking can be shown overlaid on the patient in the field of view of the user. In this case it is possible to align a structure marking shown and/or established via the medical imaging dataset with the corresponding structure of the patient.

In this way the user who is carrying out the medical examination can access information from the medical imaging dataset more quickly, ergonomically more conveniently and with a reduced susceptibility to errors.

The device for creating an augmented reality can be embodied to create a virtual screen in the field of view of the user. In particular the virtual screen can be available in any position and direction of view of the user. That is especially advantageous in relation to ergonomic aspects. In addition the restriction of the user's freedom of movement by monitors and/or the support structures is reduced.

The augmented reality information can for example feature the virtual screen. The virtual screen can for example be displayed or edited out as required. A medical dataset, in particular a medical image, examination information and/or patient information can be displayed in the virtual screen for example.

One form of embodiment of the invention makes provision for a structure of the patient to be selected based on the medical imaging dataset and for the augmented reality information to feature a structure marking, which marks the selected structure of the patient. In this way the identification of small and difficult-to-find structures of the patient is made easier.

The structure marking can for example mark an intervention area. The structure marking can further feature a representation of an intervention planning model, which relates to a planned intermediate step or to a planned result of the intervention. The intervention planning model can be established for example via a simulation. With the aid of the augmented reality information the intervention planning model can be shown overlaid on the patient. Navigation during the intervention can be improved with the intervention planning model. For example the intervention planning model can feature a planned instrument path. In this way it is also made possible for a user who has less experience in relation to a given intervention to carry out the given intervention successfully.

The intervention planning model can feature a model of an implant. The intervention planning model can be adapted for example via gesture information of the user to the structure of the patient and/or to an anatomical feature of the patient. In this way an optimum position, size and shape of the implant are able to be established.

The structure marking can for example feature a representation of a segmentation of a structure, in particular of an organ, of the patient. By way of augmented reality information for example diagnostic information, which relates to a result of a diagnosis can be shown overlaid on the patient. It is thus made possible for the user to recognize critical regions of the structure and to avoid damage during the intervention.

In accordance with one form of embodiment of the invention the patient status information is output by way of the augmented reality information. The patient status information can for example relate to a heartbeat of the patient, breathing of the patient, a patient history of the patient, a laboratory value of the patient, a demographic specification of the patient or similar. In this way the patient status information can be output in the field of view of the user. Thus an improved basis for a decision can be provided for the user, in particular a physician who is examining the patient.

The augmented reality information can feature a virtual processing tool, in particular a virtual image processing tool. For example a region of the patient can be marked by way of the virtual processing tool and/or measured by way of the virtual processing tool. In the measurement of the region of the patient for example, a position, an orientation, a form, a length, a surface, a volume of the region or similar can be established.

The augmented reality information can for example feature diagnostic information. The diagnostic information can be provided for example via a PACS dataset and/or via a CAD dataset. The diagnostic information can for example be established based on the medical imaging dataset. The medical imaging dataset can for example feature a rendered image (rendering image) and/or an unfolded image (unfolding image) of the structure of the patient, for example of a skull, of a rib cage, in particular one or more ribs, etc. The rendered image can in particular be based on user-specific rendering.

The nominal position information can for example be established based on a position of the patient during a pre-examination and/or treatment, in particular a radiation therapy treatment, which has taken place at a time before the medical examination. The reproducibility of the position of the patient can thus be improved.

In accordance with one form of embodiment of the invention the medical device is selected from the group that consists of a medical imaging device, an intervention tool, an examination device that is embodied for acquisition and/or for provision of a medical dataset, and combinations thereof.

The features that are described in relation to the medical device also apply accordingly in relation to a virtual medical device, i.e. when the term "medical device" is replaced by the term "virtual medical device" in each case in the features. The features that are described in relation to the medical examination apply accordingly in relation to a virtual medical examination, i.e. when the term "medical examination" is replaced by the term "virtual medical examination" in each case in the features. The features that are described in relation to the patient apply accordingly in relation to a virtual patient, i.e. when the term "patient" is replaced by the term "virtual patient" in each case. In this way training of medical personnel and/or planning of the medical examination can be improved. In particular a realistic training and/or a realistic planning is thus made possible even without the use of real patients and/or real medical devices.

One form of embodiment of the invention makes provision for the first user to be able to perceive their environment by way of the first augmented reality device. In particular an image of the patient and/or an avatar of the patient can be displayed to the first user instead of the real patient and/or an image of the medical device and/or a model of the medical device can be displayed to the user at the correct location instead of the real medical device. In this way a device for creating a virtual reality can also be used as an augmented reality device. A known device for creating a virtual reality is e.g. Rift from Oculus VR, LLC, USA.

One form of embodiment of the invention makes provision for the inventive system and/or for a number of components of the inventive system to be realized at least partly in the form of software on a processor system. In particular the first acquisition module, the creation module, the first output module, the information provision module, the second output module and the second acquisition module can each form a component of the inventive system and/or each be realized at least partly in the form of software on a processor system. One form of embodiment of the invention makes provision for the inventive system and/or a or a number of components of the inventive system to be realized at least partly in the form of software-supported hardware, for example FPGAs, a processor system or the like.

One form of embodiment of the invention makes provision for the inventive system and/or for a number of components of the inventive system to be formed at least partly by a Cloud via Cloud Computing. One form of embodiment of the invention makes provision for the creation module and/or at least a submodule of the creation modules to be formed by a Cloud via Cloud Computing. The Cloud can in particular feature a network of memory areas spatially remote from one another and processor systems spatially remote from one another. For data transfer from the Cloud and/or to the Cloud the first augmented reality device can feature a first Cloud interface and/or the second augmented reality device can feature a second Cloud interface.

Data can be transferred between components of the system e.g. via a suitable interface. One form of embodiment of the invention makes provision for interfaces for data transfer to and/or from components of the inventive system to be realized at least partly in the form of software. In particular the interfaces can have access facilities to suitable memory areas in which data can be suitably buffered, retrieved and updated. The interfaces can also be embodied as interfaces constructed from hardware, which can be activated by suitable software.

A largely software-based realization of an embodiment of the inventive system has the advantage that even augmented reality devices previously already used can be upgraded by a software update, in order to work in the inventive way. To this extent the object is also achieved by a corresponding computer program product with a computer program, which is able to be loaded into the memory device of a computer, wherein the steps of the inventive method can be carried out with the computer program when the computer program is executed on the computer. Such a computer program product, as well as the computer program, can include additional software components, e.g. documentation, and/or hardware components, e.g. a hardware key (dongle etc.) for use of the software.

For transport of the computer program and/or for storage of the computer program to or in an augmented reality device a computer-readable medium, for example a memory stick, a hard disk or another transportable or permanently installed data medium can be use, on which a computer program is stored, which is able to be loaded into a memory device of a computer, wherein the steps of an inventive method will be carried out with the computer program, when the computer program is executed on the computer. One form of embodiment of the invention makes provision for the first augmented reality device to feature a first computer and/or for the second augmented reality device to feature a second computer.

The first computer and/or the second computer can each feature a processor system, which e.g. features a microprocessor or a number of microprocessors working together.

In accordance with one embodiment of the invention the medical imaging device is selected from the group that consists of a C-arm x-ray device, a computed tomography device (CT device), a Single Photon Emission Computed Tomography device (SPECT device), a Positron Emission Tomography device (PET device), a Magnetic Resonance Tomography device (MRT device) and combinations thereof. In particular the medical imaging device can feature an x-ray device, an ultrasound device and similar. The medical imaging device can further be a combination of a number of imaging and/or irradiation modalities. In such cases an irradiation modality can feature an irradiation device for therapeutic irradiation for example.

Within the framework of an embodiment of the invention features that are described in relation to different forms of embodiment and/or different claim categories (method, system etc.), can be combined into further forms of embodiment. In particular the features, advantages and forms of embodiment described in relation to the inventive method are also to be transferred to the inventive system, the inventive computer program product and the inventive computer-readable medium and vice versa. In other words the device claims can also be further developed with the features that are described or claimed in conjunction with a method. Functional features of an inventive method can in such cases also be carried out by correspondingly embodied components or modules of the inventive system. The use of the indefinite article "a" or "an" does not exclude features involved also being present a number of times. It is possible for a module to feature a number of submodules separated physically from one another and for a unit to be able to feature a number of subunits separated physically from one another.

FIG. 1 shows a flow diagram of a method for outputting augmented reality information AR, which relates to a medical device 2, IT, MD and/or a medical examination of a patient 13, to a first user U1 in accordance with a first form of embodiment of the invention. In the step R1 first information is acquired that is selected from the group that consists of image information, depth information, coordinate information and combinations thereof, wherein the first information relates to the medical device 2, IT, MD and/or the medical examination of the patient 13. In the step GA augmented reality information AR, which relates to the medical device 2, IT, MD and/or the medical examination of the patient 13, is created based on the first information. In the step D1 the augmented reality information AR is output such that the augmented reality information AR is able to be perceived in the field of view of the first user U1.

Figure 2:
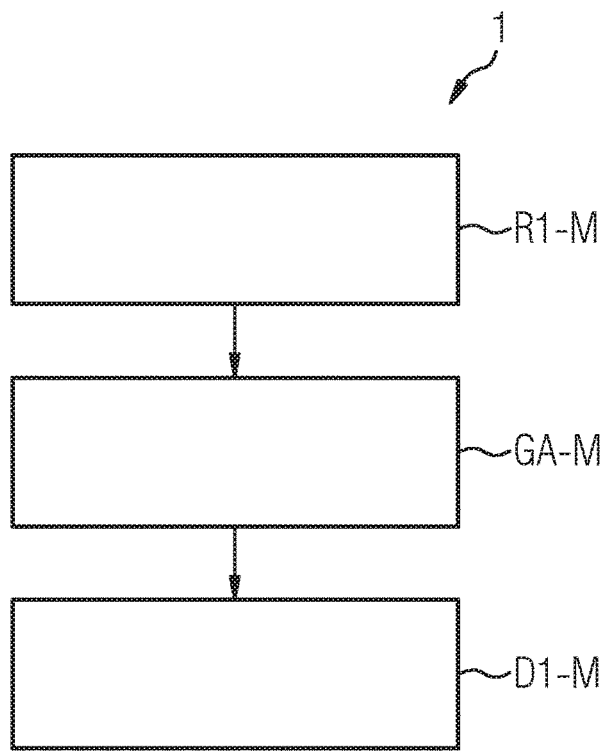
FIG. 2 shows a diagram of a system in accordance with a second form of embodiment of the invention.

FIG. 2 shows a diagram of a system 1 in accordance with a second form of embodiment of the invention. The system 1 is embodied for outputting augmented reality information AR, which relates to a medical device 2, IT, MD and/or a medical examination of a patient 13, to a first user U1 and features a first acquisition module R1-M, a creation module GA-M and a first output module D1-M. The system 1 is in particular embodied for carrying out a method in accordance with the first form of embodiment of the invention. In particular the detection R1 of the image information can be carried out via the first acquisition module R1-M, the creation GA of the augmented reality information AR via the creation module GA-M and the output D1 of the augmented reality information AR via the first output module D1-M.

Figure 3:
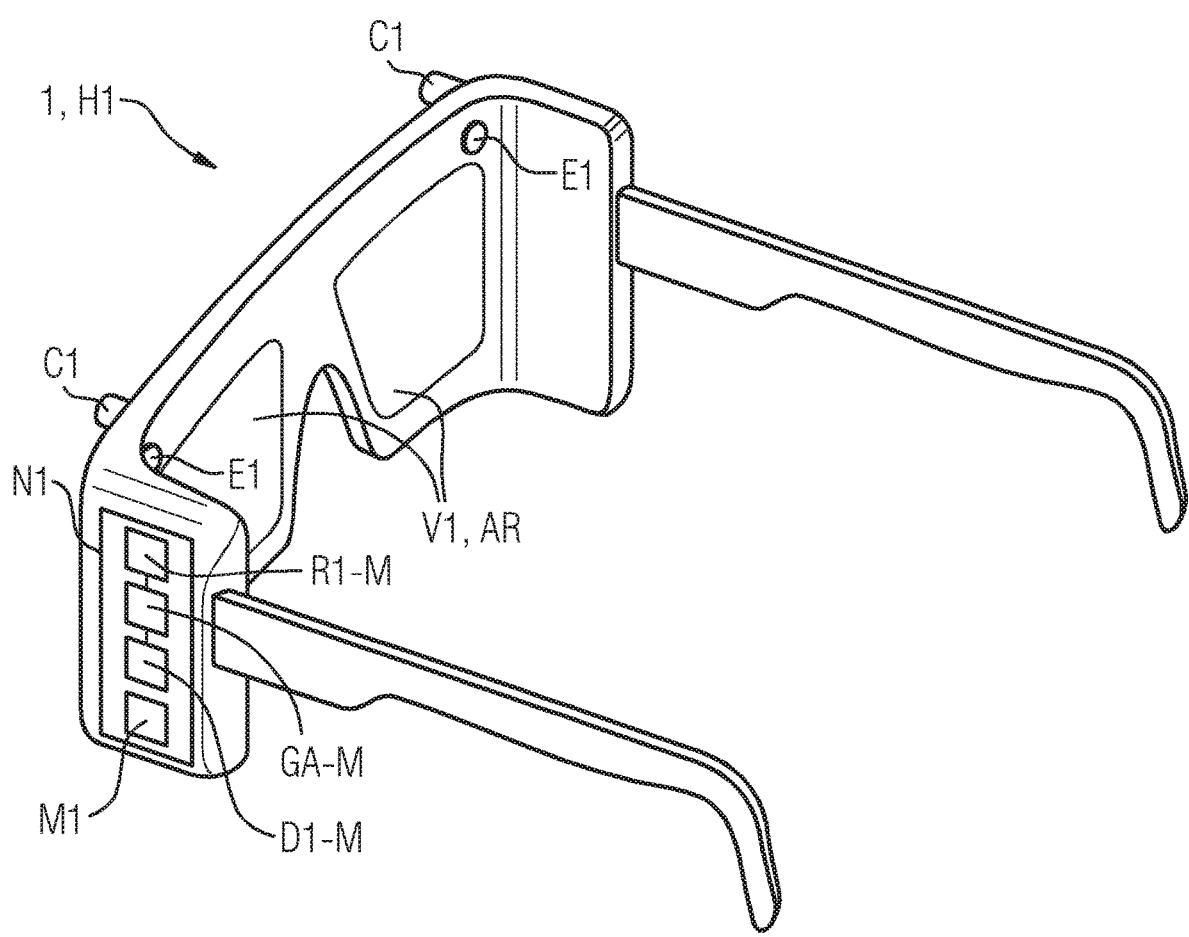
FIG. 3 shows a system in accordance with a third form of embodiment of the invention.

FIG. 3 shows a system 1 in accordance with a third form of embodiment of the invention. The system 1 features a first augmented reality device H1. The first augmented reality device H1 is embodied as data eyeglasses. The first augmented reality device H1 features a first camera unit C1, a first eye tracking unit E1, a first viewing device V1 and a first control unit N1. The first control unit N1 is a first computer, in particular a first digital computer, and is embodied for controlling the first augmented reality device H1. The first control unit N1 features the first acquisition module R1-M, the creation module GA-M and the first output module D1-M. The first control unit N1 features a first memory unit M1 and a processor system. The first memory unit M1 is embodied for loading a computer program, wherein the steps of an inventive method are carried out with the computer program when the computer program is executed on the first control unit N1. The first acquisition module R1-M, the creation module GA-M and the first output module D1-M are each realized in the form of software on the processor system of the first control unit N1. The image information and/or the depth information can be recorded via first camera unit C1. The image information and/or the depth information can be acquired via a data transfer from the first camera unit C1 to the first acquisition module R1-M. The first viewing device V1 can access a memory area of the first output module D1-M, wherein the augmented reality information can be output via a data transfer from the first output module D1-M to the first viewing device V1. The first eye tracking unit E1 is embodied for acquiring eye tracking of the first user U1. This especially enables a position and/or an orientation of the field of view of the first user U1 to be determined relative to a map dataset. In this way a position and/or an orientation relative to the field of view of the first user U1 can be determined for a real object, for example the patient 13, and/or a virtual object, for example the structure marking MI, based on a position and/or an orientation relative to the map dataset.

Figure 4:
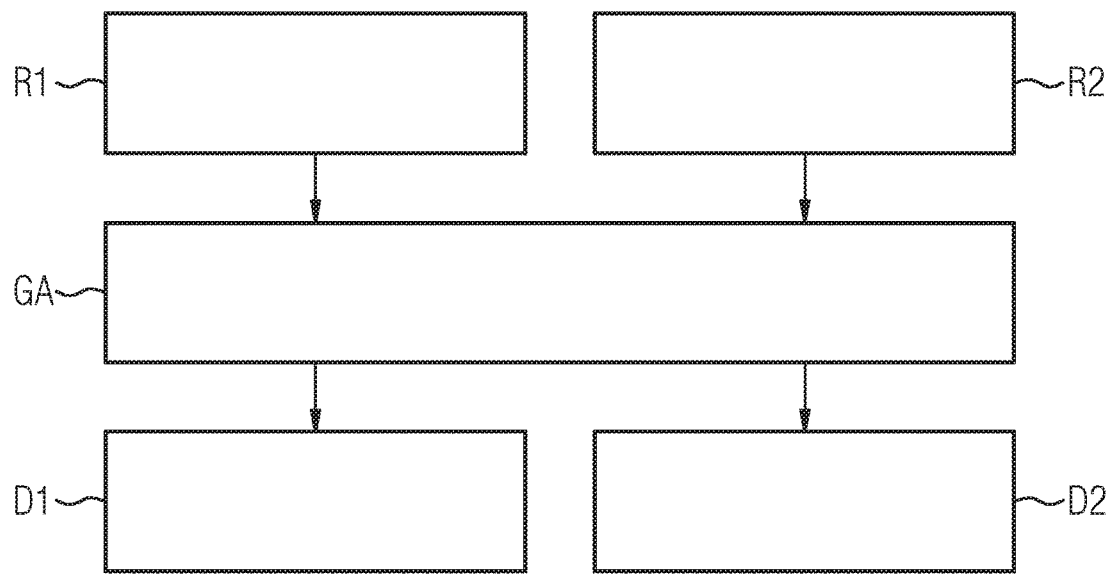
FIG. 4 shows a flow diagram of a method in accordance with a fourth form of embodiment of the invention.

FIG. 4 shows a flow diagram of a method for outputting augmented reality information AR, which relates to a medical device 2, IT, MD and/or a medical examination of a patient 13, to a first user U1 in accordance with a fourth form of embodiment of the invention. In step D2 the augmented reality information AR is output such that the augmented reality information AR is able to be perceived in a field of view of a second user U2. In step R2 an input of the second user U2 is acquired. In this case the augmented reality information AR is created based on the input of the second user U2.

Figure 5:
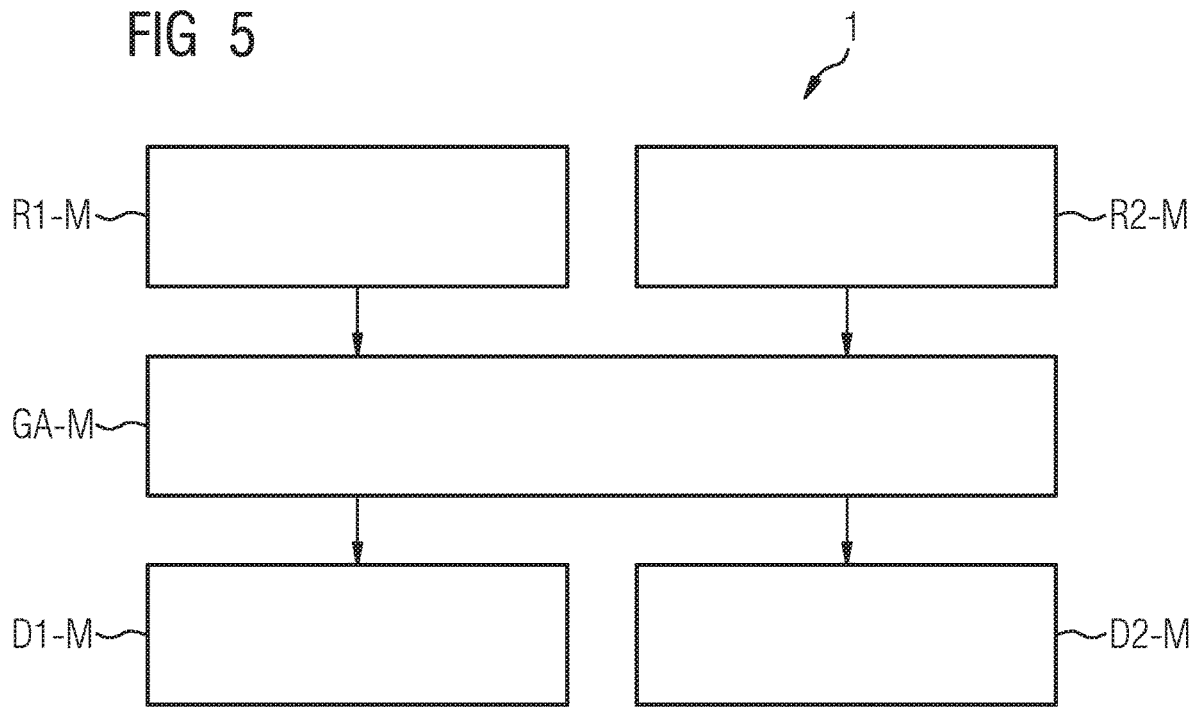
FIG. 5 shows a diagram of a system in accordance with a fifth form of embodiment of the invention.

FIG. 5 shows a diagram of a system 1 in accordance with a fifth form of embodiment of the invention. The system 1 features the first acquisition module R1-M, the creation module GA-M, the first output module D1-M, a second output module D2-M and a second acquisition module R2-M. The system 1 is in particular embodied for carrying out a method in accordance with the fourth form of embodiment of the invention. In particular the outputting D2 of the augmented reality information AR can be carried out via the second output module D2-M and the acquisition R2 of the input of the second user U2 via the second acquisition module R2-M.

Figure 6:
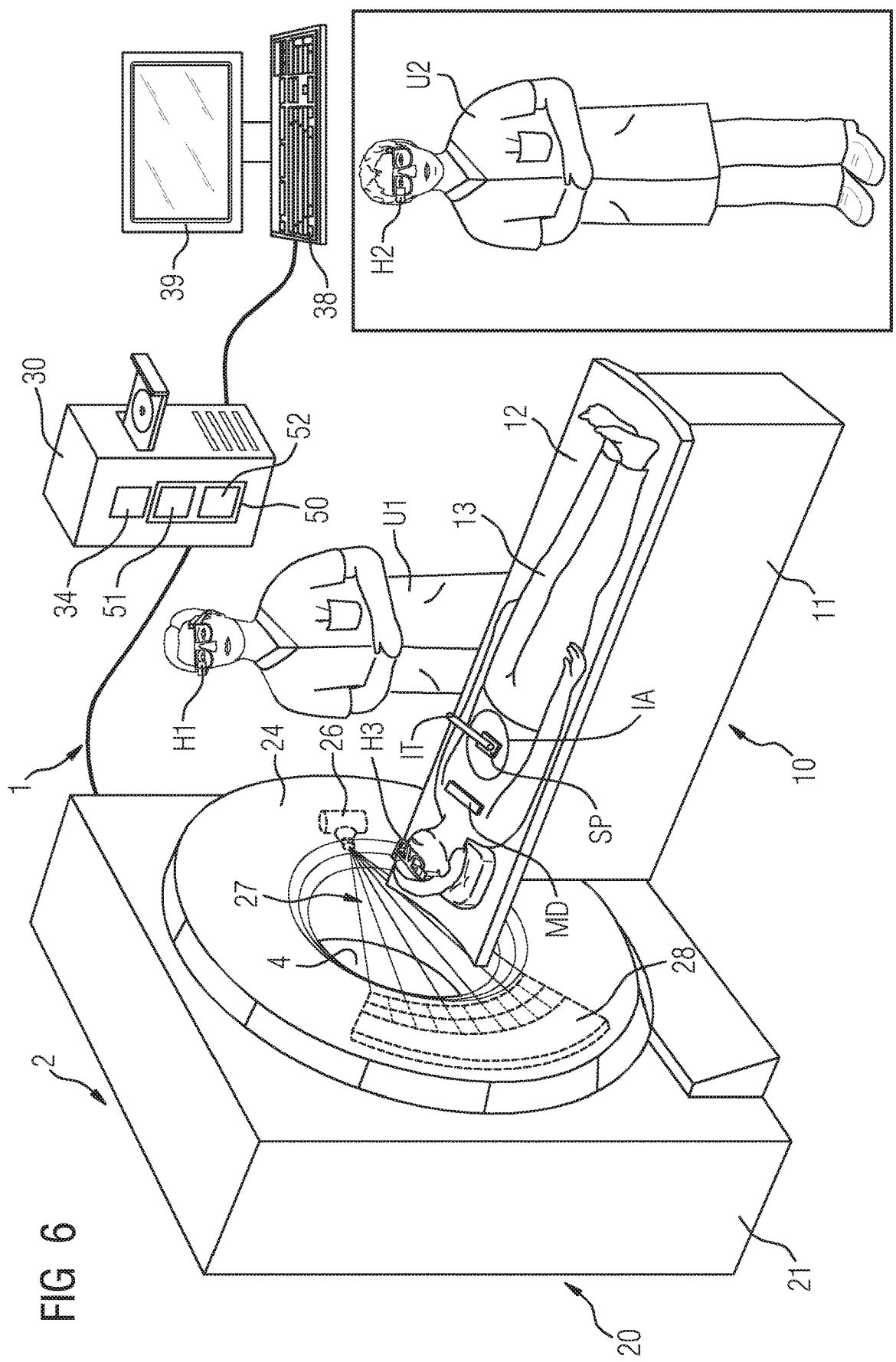
FIG. 6 shows a system in accordance with a sixth form of embodiment of the invention.

FIG. 6 shows a system 1 in accordance with a sixth form of embodiment of the invention. The system 1 features a medical imaging device 2 with an acquisition area 4 formed by a tunnel-shaped opening. Without restricting the general inventive thinking, a computed tomography device 1 is shown by way of example for the medical imaging device 2.

The medical imaging device 2 features a gantry 20, the acquisition area 4, the patient support device 10, a raw image data acquisition device 26, 28 and a control device 30. The gantry 20 features a stationary carrier frame 21 and a rotor 24. The rotor 24 is supported to allow rotation about an axis of rotation via a rotational support device. The acquisition area 4 is formed by a tunnel-shaped opening in the gantry 20. A region of an object, in particular of the patient 13, to be imaged is able to be arranged in the acquisition area 4. The patient support device 10 features a support table 11 for supporting the patient 13, wherein the transfer plate 12 is arranged movably relative to the support table 11 on the support table 11 such that the transfer plate 12 is able to be introduced into the acquisition area 4 in a longitudinal direction of the transfer plate 12.

The raw image data acquisition device 26, 28 is a projection data acquisition device 26, 28 with a radiation source 26, e.g. an x-ray source, and a detector 28, e.g. an x-ray detector. The radiation source 26 is arranged on the rotor 24 and is embodied for emission of radiation, e.g. x-ray radiation, with x-ray quanta 27. The detector 28 is arranged on the rotor 24 and is embodied for detection of the x-ray quanta 27. The x-ray quanta 27 can reach the area of the patient 13 to be imaged from the radiation source 26 and can strike the detector 28 after interacting with the area to be imaged. In this way projection data of the area to be imaged can be acquired. The projection data acquired by the projection data acquisition device 26, 28 is passed on to the control device 30. The control device 30 is embodied for controlling the medical imaging device 2. The control device 30 features an image reconstruction device 34. A medical imaging dataset can be reconstructed means of the image reconstruction device 34 based on the projection data. The medical imaging device 2 is embodied for provision of a medical imaging dataset that relates to a structure SP of the patient 13.

The medical imaging device 2 is embodied for provision of the coordinate information. The medical imaging device features a movable component 12. The control device 30 is embodied for output of a control command, which relates to a movement of the movable component 12. Without restricting the general inventive thinking, the transfer plate 12 is shown for the movable component 12. The support table 11 features a drive unit an electric motor, which is embodied for driving a movement of the transfer plate 12. The drive unit is embodied for receiving the control command and/or for driving a movement of the transfer plate 12 based on the control command. The control device 30 features a coordinate information provision unit 50 an establishment unit 51 and a movement parameter acquisition unit 52. The coordinate information provision unit 50 is embodied for providing the coordinate information. The movement parameter acquisition unit 52 is embodied for acquiring of a movement parameter, which relates to a movement of the movable component 12. The establishment unit 51 is embodied for establishing the coordinate information based on the control command and/or based on the movement parameter.

The medical imaging device 2 features an input device 38 and an output device 39. The input device 38 is embodied for inputting the control information, e.g. image reconstruction parameters and/or examination parameters. The output device 39 is for outputting control information and/or images.

The system 1 features the first augmented reality device H1 with the first control unit N1 and a second augmented reality device H2 with a second control unit. The second augmented reality device H2 is embodied as data eyeglasses. The structure and functioning of the second augmented reality device H2 essentially correspond to the structure and functioning of the first augmented reality device. Instead of the first acquisition module R1-M of the first augmented reality device H1 the second augmented reality device H2 features the second acquisition module R2-M. The second control unit, instead of the corresponding components of the first augmented reality device H1, features the second output module D2-M, a second camera unit, a second memory unit and a second viewing device V2. The sixth form of embodiment of the invention make provision for the creation module GA-M to feature a first creation submodule and a second creation submodule, for the first control unit N1 to feature the first creation submodule and for the second control unit to feature the second creation submodule. The first control unit N1, the second control unit and the control device 30 are connected to one another via a data transmission device, in particular wirelessly. In particular a data transfer is able to be realized between the modules of the first control unit N1, the modules of the second control unit and the control device 30 via the data transfer device. A control of the medical imaging device 2 by way of the first augmented reality device H1 and/or by way of the second augmented reality device H2 is thus optionally able to be realized. In particular a control command, which relates to a movement of the movable component 12, can be output by way of the first augmented reality device H1 and/or by way of the second augmented reality device H2. In particular the first augmented reality device H1 and/or the second augmented reality device H2 can feature the establishment unit 51. Optionally the control device 30 can form a third creation submodule of the creation module GA-M.

The first augmented reality device H1 is worn by a first user U1. The second augmented reality device H2 is worn by a second user U2. Optionally a third augmented reality device H3 is worn by the patient 13. With the third augmented reality device H3 the planned part steps and the results to be expected can be explained by displaying them to the patient 13 for example in preparation for the intervention and/or during imaging preparing for an intervention breathing instructions as well as calming sequences of images can be output.

By way of the first acquisition module R1-M first information can be acquired, which is selected from the group that consists of image information, depth information, coordinate information and combinations thereof, wherein the first information relates to the medical device 2, IT, MD and/or the medical examination of the patient 13. The first information relates to a spatial area in a field of view of the first user U1. The spatial area in particular comprises the intervention area IA. Without restricting the general thinking of the invention, the medical imaging device 2, the examination device MD and the intervention tool IT are shown by way of example for the medical device in each case. Without restricting the general thinking of the invention, an intervention is shown by way of example for the medical examination. An intervention tool IT, for example a scalpel, is used for the intervention. In this case it is a matter of the correct position of the intervention tool IT relative to the structure SP of the patient 13. The intervention is carried out by the first user U1. The second user U2 is located outside the examination room in which the medical imaging device 2 is arranged and in which the intervention is taking place. The system 1 makes possible in particular the guidance of the first user U1 by the second user U2 in relation to the correct position of the intervention tool IT relative to the structure SP of the patient 13.

Figure 7:
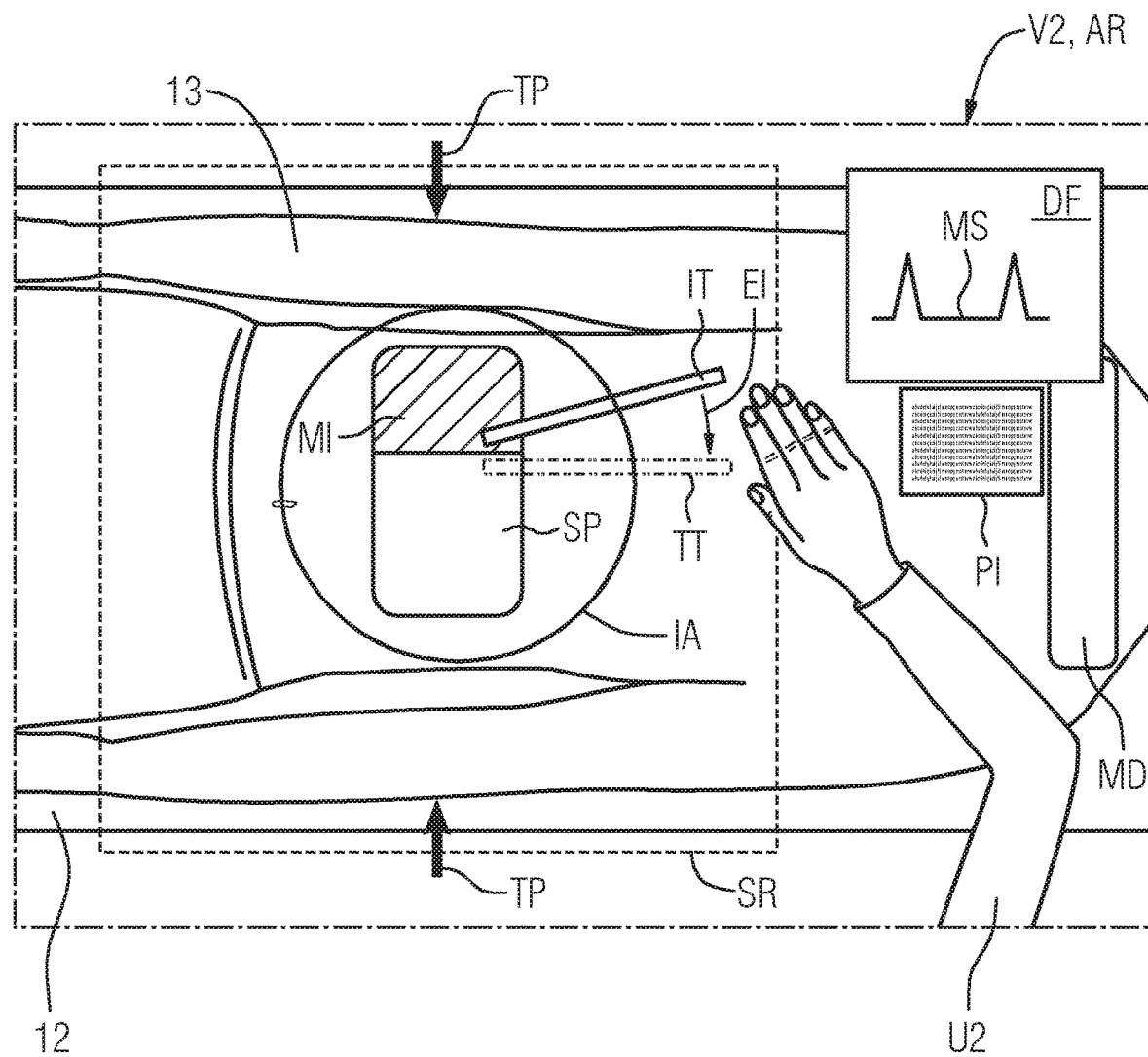
FIG. 7 shows a section from the field of view of the second user, wherein the field of view is enhanced with the augmented reality information.

FIG. 7 shows a section from the field of view of the second user U2, wherein the field of view of the second user U2 is enhanced with the augmented reality information AR. A part of the field of view of the first user U1 is shown in the field of view of the second user U2 such that the second user U2 sees the patient 13, the intervention tool IT and the transfer plate 12 from the perspective of the first user U1. The augmented reality information AR is shown in the field of view of the second user U2 such that the second user U2 sees the augmented reality information AR from the perspective of the first user U1.

The section from the field of view of the second user U2 shown in FIG. 7 thus differs from a corresponding section from the field of view of the first user U1 in that the patient 13, the patient support device 10, the intervention tool IT are visible as an image and/or as a model for the second user U2 and that the arm of the second user U2 is visible as an image and/or as a model for the first user U1.

Based on the first information, examination information, which relates to a position of an intervention tool IT relative to the structure SP of the patient 13, is established. The augmented reality information AR is created based on the examination information such that the augmented reality information AR features a marking EI, which represents the movement of the intervention tool IT to be carried out as the next movement, for example in the form of a moving stereoscopic and/or hologram-type representation of the intervention tool IT.

In accordance with the sixth form of embodiment of the invention the system 1 features an examination device MD. The augmented reality information AR is created based on a medical signal, for example an EKG signal provided by the examination device MD, such that the augmented reality information AR features a signal output field DF, wherein the medical signal is shown in the signal-output field DF as a timing characteristic.

In preparation for the intervention the patient 13 is identified automatically by way of the first augmented reality device H1, in that patient identification information is established based on an image of the patient 13, for example with the aid of biometric features. Based on the patient identification information the augmented reality information AR is created such that personal patient data and data which relates to the patient history of the patient 13 will be shown in a patient data output field PI.

Patient position information will be established based on the first information. The augmented reality information AR is created based on the patient position information such that the position of the augmented reality information AR is determined relative to the field of view of the first user U1 based on the position of the patient 13. In particular the augmented reality information AR is shown overlaid anatomically correctly on the patient 13.

The creation module GA-M is embodied for creating the augmented reality information AR based on the medical imaging dataset. The medical imaging dataset relates to the structure SP of the patient 13. The structure SP can for example be an organ of the patient 13. The augmented reality information AR features a structure marking MI, which marks the structure SP of the patient 13. The structure marking MI is shown overlaid anatomically correctly on the structure SP. The structure marking MI is designed so that a first part area of the structure SP is able to be distinguished from a second part area of the structure SP via the structure marking MI. In FIG. 7 the first part area of the structure SP is shown as a cross-hatched surface and the second part area of the structure SP is shown as a white surface. For example the first part area can involve a part of the organ to be removed and/or the second part area a remaining part of the organ. In this way the first user U1 and the second user U2 can recognize the first part area of the structure SP and/or the second part area of the structure SP quickly and exactly.

The augmented reality information AR features the nominal position marking TP, which relates to the nominal position of the patient 13 on the transfer plate 12. The reproducibility between a number of medical imaging datasets, which are recorded after different part steps of the intervention, is improved.

The augmented reality information AR features the nominal position marking TT, which relates to the nominal position of the intervention tool IT. The nominal position marking TT is provided in that the second user U2 creates a model of the intervention tool IT by way of the second augmented reality device H2 and positions the model of the intervention tool IT in the nominal position of the intervention tool IT. The second augmented reality device H2 is embodied to recognize gestures of the second user U2 and to create the augmented reality information AR based on the gestures.

The augmented reality information AR features a region marking SR, which marks the region of the transfer plate 12, which is selected in accordance with the selected protocol for imaging via the medical imaging device 2. Thus the region marking SR also marks the region of the patient 13 that is selected, for an unchanged position of the patient 13 relative to the transfer plate 12, for the imaging via the medical imaging device 2. The structure marking SP, the nominal position marking TP, the nominal position marking TT and the region marking SR each feature a stereoscopic representation and/or a hologram-type representation, Literature Reference

[CR06] Ozan Cakmakci and Jannick Rolland: "Head-Worn Displays: A Review". JOURNAL OF DISPLAY TECHNOLOGY, VOL. 2, NO. 3, SEPTEMBER 2006, the entire contents of which are hereby incorporated herein by reference.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for outputting augmented reality information to a user, the method comprising:
    acquiring a medical imaging dataset relating to an anatomical structure of a patient;
    acquiring first information, the first information including one or more of image information, depth information, and coordinate information;
    creating the augmented reality information by evaluating, via a machine learning algorithm, the first information and the medical imaging dataset, the augmented reality information including a structure marking, including a 3-dimensional (3D) image marking the anatomical structure of the patient; and
    outputting the augmented reality information in response to the user placing the anatomical structure of the patient in a field of view of the user, the augmented reality information being combined, in an anatomically correct manner, with the anatomical structure of the patient and being perceivable in the field of view of the user.

2. The method of claim 1, wherein a control command, relating to a movement of a movable component of a medical device, is output.

3. The method of claim 1, wherein examination information, relating to a medical examination of the patient, is established based on the first information, and wherein the augmented reality information is created based on the examination information.

4. The method of claim 1, wherein patient information, relating to the patient, is established based on the first information, and wherein the augmented reality information is created based on the patient information.

5. The method of claim 1, wherein the first information relates to at least one of a medical device and a medical examination of the patient, wherein nominal position information, relating to at least one of a nominal position of the patient and a nominal position of the medical device, is provided, wherein the augmented reality information is created based on the nominal position information, and wherein the augmented reality information includes a nominal position marking, marking the nominal position of at least one of the patient and the medical device.

6. The method of claim 5, wherein the augmented reality information includes the structure marking, the nominal position marking and a movement marking.

7. The method of claim 1, wherein the first information relates to at least one of a medical device and a medical examination of the patient, wherein region information, relating to a region of at least one of the patient and the medical device, is provided, wherein the augmented reality information is created based on the region information, and wherein the augmented reality information includes a region marking, marking the region of at least one of the patient and the medical device.

8. The method of claim 7, wherein the augmented reality information includes the structure marking, the region marking and a movement marking.

9. The method of claim 1, further comprising:
outputting the augmented reality information to be perceivable in a field of view of a second user; and
acquiring an input of the second user, wherein the creating includes creating the augmented reality information using the input of the second user.

10. The method of claim 1, wherein the first information relates to at least one of a medical device and a medical examination of the patient, wherein region information, relating to a region of at least one of the patient and the medical device, is provided, wherein the augmented reality information is created based on the region information, and wherein the augmented reality information features a region marking, which marks the region of at least one of the patient and the medical device.

11. The method of claim 1, wherein the acquiring of the medical image dataset relating to an anotomical structure of a patient is achieved via a computed tomography (CT) scan of the patient.

12. The method of claim 11, wherein the acquiring of the first information includes acquiring information of the patient via an optical camera.

13. The method of claim 1, wherein the acquiring of the first information includes acquiring information of the patient via an optical camera.

14. The method of claim 13, wherein the augmented reality information includes the structure marking and a movement marking.

15. The method of claim 14, wherein the movement marking illustrates a location for an intervention tool in relation to a portion of the anatomical structure.

16. The method of claim 13, wherein the acquiring includes acquiring the first information from the medical imaging dataset.

17. The method of claim 1, wherein the first information relates to at least one of a medical device and a medical examination of the patient.

18. The method of claim 1, wherein the outputting of the augmented reality information includes overlaying augmented reality information, in the anatomically correct manner, over anatomical structure of the patient, the augmented reality information overlaid being perceivable in the field of view of the user.

19. The method of claim 1, wherein the augmented reality information includes the structure marking and a movement marking.

20. The method of claim 19, wherein the movement marking illustrates a location for an intervention tool in relation to a portion of the anatomical structure.

21. The method of claim 1, wherein the acquiring includes acquiring the first information from the medical imaging dataset.

22. A system for outputting augmented reality information, relating to at an anatomical structure of a patient, to a first user, comprising:
at least one memory and at least one processor, the at least one memory containing computer readable code that, when executed by the at least one processor, configures the at least one processor to,
acquire a medical imaging dataset relating to an anatomical structure of the patient,
acquire first information, the first information including one or more of image information, depth information, and coordinate information,
create the augmented reality information by evaluating, via a machine learning algorithm, the first information and the medical imaging dataset, the augmented reality information including a 3-dimensional (3D) image marking, marking the anatomical structure of the patient, and
output the augmented reality information in response to the first user placing the anatomical structure in a field of view of the first user, the augmented reality information being combined, in an anatomically correct manner, with the anatomical structure of the patient and being perceivable in the field of view of the first user.

23. The system of claim 22, further comprising:
a medical device, wherein the medical device is embodied to provide the coordinate information.

24. The system of claim 23, wherein the medical device includes a movable component and the system further comprises:
a control device configured to,
acquire a movement parameter, relating to a movement of the movable component, and
establish the coordinate information based on the movement parameter.

25. The system of claim 22, wherein the at least one processor is further configured to,
output the augmented reality information to be perceivable in a field of view of a second user,
acquire an input of the second user,
wherein the at least one processor, configured to create the augmented reality information, includes creating the augmented reality information using the input of the second user.

26. The system of claim 22, further comprising:
a first augmented reality device, including a first processor of the at least one processor.

27. The system of claim 22, wherein the augmented reality information includes the 3-dimensional image marking, and a movement marking.

28. The system of claim 27, wherein the movement marking illustrates a location for an intervention tool in relation to a portion of the anatomical structure.

29. The system of claim 22, wherein the at least one processor, configured to acquire the first information, includes acquiring the first information from the medical imaging dataset.

30. The system of claim 22, wherein the at least one processor, configured to acquire the first information, includes acquiring information of the patient via an optical camera.

31. The system of claim 30, wherein the at least one processor, configured to acquire the medical image dataset relating to an anotomical structure of a patient, includes acquiring the medical image dataset via a computed tomography (CT) scan of the patient.

32. The system of claim 22, wherein the at least one processor, configured to acquire the medical image dataset relating to an anatomical structure of a patient, includes acquiring the medical image dataset via a computed tomography (CT) scan of the patient.

33. The system of claim 22, wherein the augmented reality information includes the 3-dimensional (3D) image marking, and a movement marking.

34. A non-transitory computer-readable medium, including a computer program, the computer program being loadable into a memory device of a computer, the computer program being configured to execute the method of claim 1 when the computer program is executed on the computer.

35. A non-transitory memory storing a computer program, the computer program being configured to execute the method of claim 1 when the computer program is executed on a computer.

* * * * *